United States Patent [19]
Johnson et al.

[11] Patent Number: 4,882,433
[45] Date of Patent: Nov. 21, 1989

[54] 3'-PYRIDINYLALKYLINDEN- AND 3'-PYRIDINYLALKYLINDOL-2-CARBOXYLIC ACIDS AND ANALOGS

[75] Inventors: Roy A. Johnson, Kalamazoo; Chiu-Hong Lin, Portage, both of Mich.

[73] Assignee: The Upjohn Company, Kalamazoo, Mich.

[21] Appl. No.: 174,265

[22] Filed: Mar. 28, 1988

Related U.S. Application Data

[60] Division of Ser. No. 85,103, Jun. 29, 1987, Pat. No. 4,767,865, which is a continuation of Ser. No. 792,903, Oct. 30, 1985, abandoned.

[51] Int. Cl.$^4$ .................. C07D 401/06; C07D 401/12
[52] U.S. Cl. ..................................... 546/273; 546/342
[58] Field of Search .......................................... 546/273

[56] References Cited

U.S. PATENT DOCUMENTS

| | | | |
|---|---|---|---|
| 4,410,539 | 10/1983 | Cross et al. | 514/397 |
| 4,447,620 | 5/1984 | Sih et al. | 548/336 |
| 4,452,986 | 6/1984 | Johnson et al. | 548/336 |
| 4,455,427 | 6/1984 | Johnson | 546/269 |
| 4,490,531 | 12/1984 | Johnson | 546/269 |
| 4,495,357 | 1/1985 | Johnson | 546/269 |

Primary Examiner—Alan L. Rotman
Attorney, Agent, or Firm—Lawrence T. Welch; Donald L. Corneglio

[57] ABSTRACT

The present invention provides novel 3'-pyridinylalkenylindole-2-carboxylic acids and derivatives thereof of the formulas I and II

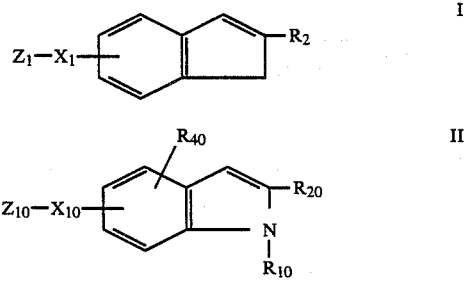

which are useful as thromboxane A$_2$ (TXA$_2$) synthetase inhibitors and as such represent potent pharmacological agents.

7 Claims, No Drawings

3'-PYRIDINYLALKYLINDEN- AND 3'-PYRIDINYLALKYLINDOL-2-CARBOXYLIC ACIDS AND ANALOGS

This application is a division of Ser. No. 085,103 filed June 29, 1987, now U.S. Pat. No. 4,767,865 which in turn is a continuation of Ser. No. 792,903, filed Oct. 30, 1985, now abandoned.

BACKGROUND OF THE INVENTION

The present invention relates to novel compositions of matter. More particularly, the present invention relates to pyridyl substituted indenes and indoles. These compounds are potent thromboxane A$_2$ inhibitors and as such represent useful pharmacological agents.

Since the discovery that human platelets convert the prostaglandin endoperoxide (PGH$_2$) into a labile proaggregatory molecule known as thromboxane A$_2$ (TXA$_2$), researchers have sought compounds that could selectively inhibit the biological activity of TXA$_2$. This end may be achieved in two different ways: the synthesis of TXA$_2$ can be blocked by inhibiting the TXA$_2$ synthetase, or a compound could be a receptor level antagonist of TXA$_2$. As therapeutic agents, TXA$_2$ synthetase inhibitors are more useful. See, e.g., R. Gorman, "Biological and Pharmacological Evaluation of Thomboxane Synthetase Inhibitors," Advances in Prostaglandin and Thromboxane Research, 6: 417 (1980), and references cited therein. Most important are compounds which selectively inhibit TXA$_2$ synthetase. Id.

A number of TXA$_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)1H-imidazole] disclosed in D. Harris, et al., Advances in Prostaglandin and Thromboxane Research 6: 437 (1980); pyridine and its derivatives, disclosed in T. Miyamoto, et al., Advances in Prostaglandin and Thromoboxane Research, 6: 443 (1980), and British patent application 2,039,903A (abstracted in Derwent Farmdoc No. 50111C (1980)). See also H. Tai, et al., Advances in Prostaglandin and Thromboxane Research, 6: 447 (1980). Other compounds which have been disclosed as thromboxane synthetase inhibitors, include sodium p-benzyl-4(1-oxo-2-(4-chlorobenzyl)-3-phenylpropyl)phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

INFORMATION DISCLOSURE STATEMENT

U.S. Pat. No. 4,410,539 discloses certain imidazolyl- and pyridinyl-substituted benzofurans, benzothiophenes, and indoles which are stated to be thromboxane synthetase inhibitors. No pyridinyl-substituted indoles are actually named therein. U.S. Pat. Nos. 4,452,986 and 4,447,620 disclose imidazolyl-substituted benzofurans and benzothiophenes, respectively, as thromboxane synthetase inhibitors. U.S. Pat. Nos. 4,495,357; 4,490,531; and 4,455,427 all disclose certain pyridinyl substituted benzofurans as thromboxane synthetase inhibitors. Copending applications 715,595 and 715,597, both filed Mar. 25, 1985, disclose pyridinyl-substituted benzothiophenes.

SUMMARY OF THE INVENTION

The present invention particularly provides:
a compound of the formula I wherein $Z_1$ is
(a) 4-pyridinyl,
(b) 3-pyridinyl, or
(c) 1-imidazolyl;
wherein $X_1$ is
(a) —(CH$_2$)$_n$—,
(b) —O—,
(c) —CH$_2$O—, or
(d) —OCH$_2$—;
wherein $R_1$ is
(a) hydrogen,
(b) a pharmacologically acceptable cation, or
(c) (C$_1$–C$_{12}$) alkyl;
wherein $R_2$ is
(a) —COOR$_1$,
(b) CH$_2$OH,
(c) —CON(R$_3$)$_2$,
(d) —CN, or
(e) —CH$_2$N(R$_3$)$_2$;
wherein $R_3$ is
(a) hydrogen, or
(b) (C$_1$–C$_4$)alkyl;
wherein n is an integer from 0 to 2, inclusive; or a pharmacologically acceptable acid addition salts thereof.

The present invention also provides:
A compound of the formula II:
wherein $Z_{10}$ is
(a) 4-pyridinyl, or
(b) 3-pyridinyl;
wherein $X_{10}$ is:
(a) —(CH$_2$)$_n$—, or
(b) —CH$_2$NH—;
wherein $R_{10}$ is:
(a) hydrogen,
(b) methyl, or
(c) benzyl;
wherein $R_{20}$ is:
(a) hydrogen,
(b) COOR$_3$,
(c) CH$_2$OH,
(d) CON(R$_5$)$_2$,
(e) CH$_2$N(R$_5$)$_2$,
(f) CN, or
(g) COR$_5$;
wherein $R_{30}$ is:
(a) hydrogen,
(b) a pharmacologically acceptable cation, or
(c) (C$_1$–C$_4$)alkyl;
wherein $R_{40}$ is:
(a) (C$_1$–C$_4$)alkyl,
(b) chloro,
(c) bromo,
(d) OCH$_3$, or
(e) hydrogen;
wherein $R_{50}$ is:
(a) hydrogen, or
(b) (C$_1$–C$_4$)alkyl;
wherein n is an integer from 0 to 2; or a pharmacologically acceptable salt thereof.

The carbon atom content of various hydrocarbon-containing moieties is indicated by a prefix designating the minimum and maximum number of carbon atoms in the moiety, i.e., the prefix (Ci-Cj) indicates a moiety of the integer "i" to the integer "j" carbon atoms, inclusive. Thus (C1-C3)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, athough cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzyla-mine, dibenzylamine, α-phenylethylamine, β-phenylethylamine, ethyl-enediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
 1-methylpiperidine,
 4-ethylmorpholine,
 1-isopropylpyrrolidine,
 2-methylpyrrolidine,
 1,4-dimethylpiperazine,
 2-methylpiperidine,
and the like, as well as amines containing water-solubilizing or hydrophilic groups, e.g.,
 mono-, di-, and triethanolamine,
 ethyldiethanolamine,
 N-butylethanolamine,
 2-amino-1-butanol,
 2-amino-2-ethyl-1,3-propanediol,
 2-amino-2-methyl-1-propanol,
 tris(hydroxymethyl)aminomethane,
 N-phenylethanolamine,
 N-(p-tert-amylphenyl)diethanolamine,
 glactamine,
 N-methylglycamine,
 N-methylglucosamine,
 ephedrine,
 phenylephrine,
 epinephrine,
 procaine,
and the like. Further useful amine salts are the basic amino acid salts, e.g.,
 lysine and
 arginine.
Examples of suitable pharmacologically acceptable quaternary ammonium cations are
 tetramethylammonium,
 tetraethylammonium,
 benzyltrimethylammonium,
 phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as indenes (formula I) or as indoles (formula II), using the Chemical Abstracts numbering system (see Naming and Indexing of Chemical Substances for Chemical Abstracts during the Ninth Collective Period (1972–1976), a reprint of section IV from the Volume 76 Index Guide.)

Certain of the indene compounds of the present invention were demonstrated to inhibit Thromboxane $A_2$ biosynthesis in platelet rich plasma. In this system, 6-(3-pyridylmethyl)indene-2-carboxylic acid inhibited thromboxane synthetase 95% as compared to control at 1 μg/ml. Certain of the indoles of the present invention were shown to inhibit $TXA_2$ as follows:

Potential inhibitors were tested by comparing the response of the rabbit aorta to the amount of $TXA_2$ produced by mixing PGH2 and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, one compound, 5-[(3-pyridinylmethyl)amino]-1H-indole-2-carboxylic acid, sodium salt, exhibited an approximate $ED_{50}$ of less than 1 μg/ml but greater than 100 ng/ml.

Certain of the ester compounds claimed herein exhibit low $TXA_2$ synthetase inhibitory activity in these in vitro systems, but are active $TXA_2$ synthetase inhibitors in vivo.

All the novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72897B; 63409B; 037568C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 400 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg to about 500 µg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straightchain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane sythetase inhibitor have both been shown to be effective in controlling tumor cell metastasis, see, e.g., K. Honn, et al., "Thromboxane Synthetase Inhibitors and Prostacyclin Can Control Tumor Cell metastasis," an Abstract of the Twentieth Annual Meeting of the American Society for Cell Biology, in the Journal of Cell Biology, 87: 64 (1980).

Similarly, prostacyclin has been shown to be an effective antihypertensive agent. The compounds of the present invention are also used for this purpose. (See, e.g., British patent specification 2,039,903A).

For a general discussion of the utility of $TXA_2$ synthetase inhibitors which increase endogenous prostacyclin, see, Aiken, et al. J. Pharmacol. Exp. Ther., 219: 299 (1981).

The compounds of the present invention are prepared by the method depicted in Chart A.

The synthetic route used to prepare the indene compounds is outlined in Chart A. In Chart A, $R_{11}$ is a sodium ion or ethyl. The starting point is cinnamic acid derivative A-1. Catalytic reduction saturates the double bond of A-1 giving ester A-2, wherein $R_{11}$ is ethyl. The ester is saponified and the sodium salt ($R_{11}$ is sodium) is used for cyclization to the indanonne A-3. Cyclization in polyphosphoric acid gives A-3.

The enolate of ketone A-3 is acylated with diethyl carbonate following a procedure described by House and Hudson for the acylation of similar indanones (J. Org. Chem. 35: 647 (1970)). The Keto-ester A-4 is thereby obtained.

The sodium borohydride reduction of keto-ester A-4 varies dramatically depending on the solvent used. Entirely different results are seen by TLC depending on whether a mixture of ether-water or ethanol is used. The former solvent combination gives reduction to a mixture of the desired hydroxy-ester epimers (A-5) in nearly equal amounts. The two compounds are separated by chromatography.

The reaction of either A-5 epimer with thionyl chloride gives similar mixtures of three new compounds (the 2 epimers of A-6, and the compound of A-7, where $R_{11}$ is ethyl). To prepare olefin A-7 from chloro-esters (A-6), the mixture obtained from the preceding reaction is warmed with 1,5-diazabicyclo[4.3.0]non-5-ene (DBN) in benzene for an hour after which elimination is complete. Formulas A-7 and A-7A depict both the 5- and 6-substituted indenes. These isomers may be prepared by starting with the appropriate formula A-2 compound or, the 6-substituted isomer may be treated with a base such as sodium hydride, or potassium hydride, and the resultant mixture separated chromatographically.

Hydrolysis of A-7 or A-7A (where $R_{11}$ is ethyl) with an equivalent of sodium hydroxide in methanol-water gives a mixture of acid and methyl ester. Additional base and water were required for complete hydrolysis and after acidification (to pH 6.4), the crystalline acid (where $R_{11}$ is hydrogen) is obtained.

The indoles of the present invention are prepared as depicted in Charts B and C. In Chart B, an aldehyde of the formula B-1 is reacted with the formula B-2 indole to yield the formula B-3 ester which is converted to the corresponding salts, esters, and amides by means known in the art.

In Chart C, a modification of the Japp-Klingemann reaction (Chem. Ber. 20: 2942 (1887)), in which hydrazones are derived from the reactionn of aryl diazonium salts with 2-alkyl-3-oxobutyric acid esters, is used. Subsequent Fisher indole cyclization conditions convert the hydrazone into an indole. The diazonium salt C-1 is allowed to react with ethyl 2-methyl-3-oxobutyrate in order to produce the hydrazone. Cyclization of C-2 to the indole-2-carboxylic acid ester C-3 requires only mild warming (90° C. for 10 min) in polyphosphonic acid. Higher temperatures or longer heating greatly diminished the yield. Saponification of C-3 with one equivalent of sodium hydroxide gives the sodium salt.

Analogous chemical procedures are described in U.S. Pat. Nos. 4,410,539; 4,452,986; 4,447,620; 4,495,357; 4,490,531; and 4,455,427; all of which are expressly incorporated by reference herein.

Thus, all of the compounds of the present invention are prepared by the methods described above or by means well known in the art, using analogous procedures and known starting materials.

DESCRIPTION OF THE PREFERRED EMBODIMENTS

The present invention is seen more fully by the Examples given below.

PREPARATION 1

Refer to Chart A (Conversion of A-1 to A-2).

A solution of the corresponding olefin (4.06 g, 0.015 mol) in absolute ethanol (50 ml) with 5% palladium/-carbon (1.0 g) is hydrogenated at atmospheric pressure for 4.25 hours. The reaction mixture is filtered and the solvent is removed under reduced pressure to yield a colorless oil. The product is combined with the material obtained in a 1.74 mmol experiment and chromatographed on three Merck size B columns and eluted with 2.3 L of 20% acetone-hexane and then with 25% acetone-hexane. Fractions which contain 25 ml each are collected. The product is obtained in fractions 59-92 to yield 3.42 g (76% of theory) of a colorless oil; $^1$H NMR ($\delta$ CDCl$_3$) 8.52, 7.70-6.91, 4.14, 3.93, 2.93, and 1.22; mass spectrum, M+ at 269, other ions at 224, 196. 182, 167 m/e; IR (liquid olefin) 2981, 1733, 1608, 1590, 1575, 1514, 1479, 1423, 1373, 1296, 1255, 1183, 1157, 1027, 804, 789, 713 cm$^{-1}$. Anal. Calc'd for C$_{17}$H$_{19}$NO$_2$: C, 75.81; H, 7.11; N, 5.20. Found: C, 75.35; H, 7.25; N, 5.17. TLC (silica gel, 50% ethyl acetate/hexane): starting material Rf=0.52; product Rf=0.59.

PREPARATION 2

3-[4-(3'-Pyridylmethyl)phenyl]propionic acid, Sodium Salt

Refer to Chart A (conversion of A-2 to A-3).

The ester of Preparation 1 is dissolved in methanol (16 ml) and then 1.0N NaOH (13 ml) is added. The solution is stirred at room temperature and the reaction is found to be complete by TLC after four hours. The methanol is removed under reduced pressure. The aqueous residue is frozen in a dry ice-acetone bath and then lyophilized overnight. A white powder is obtained (3.03 g); $^1$H NMR ($\delta$ D$_2$O) 8.30, 7.75-6.82, 3.79, and 2.37.

PREPARATION 3

6-(3-Pyridylmethyl)-1-indanone

Refer to Chart A (conversion of A-3 to A-4).

Polyphosphoric acid (20 g) is preheated to 95° C. under a nitrogen atmosphere. The sodium salt of Preparation 2 (4.55 g, 0.017 mol) is added as a dry solid. The viscous mixture is stirred thoroughly with a glass rod periodically during the reaction. The reaction appears to be complete by TLC after 6.5 hours.

The reaction is cooled and water added. The mixture is made slightly basic with 50% sodium hydroxide with vigorous stirring and ice bath cooling (pH 7 to 8). The aqueous mixture is extracted well with ethyl acetate (4 times). The pooled ethyl acetate extracts are washed with half-saturated brine, dried (NA$_2$SO$_4$), filtered, and evaporated to give a dark red oil. The oil is chromatographed on 394 g of silica gel (40-63 $\mu$m) using 40% acetone-methylene chloride to elute the product. A colorless oil (1.56 g, 41% of theory) which crystallizes is obtained. The oil is crystallized from acetonehexane to give 1.21 g of colorless crystals, mp 105°-107° C.

A sample is recrystallized for analysis, giving colorless crystals, mp 106.5°-107° C. $^1$H NMR ($\delta$ CDCl$_3$) 8.60, 7.82-7.04, 3.12 and 2.71; mass spectrum, M+ at 223 (100%) other ions at 194, 181, 167 m/e; IR (nujol mull) 1696, 1653, 1612, 1588, 1489, 1443, 1427, 1289, 1158, 1103, 1026, 825, 809, 735, 719 cm$^{-1}$. Anal. Calcd. for C$_{15}$H$_{13}$N-O: C, 80.69; H, 5.87; N, 6.27. Found: C, 80.46; H, 5.95; N, 6.13.

PREPARTION 4

2-Carboxyethyl-6-(3-pyridylmethyl)-1-indanone

Refer to Chart A (conversion of A-4 to A-5).

To a warm (60° C.) suspension of sodium hydride (541 mg of a 59.6% dispersion, 13.4 mmol NaH) in toluene (15 ml) with diethylcarbonate (7.8 ml, 7.6 g, 65 mmol) under a N$_2$ atmosphere, is added the ketone of Preparation 3 (1.20 g, 5.37 mmol) in toluene (15 ml) dropwise over a 5 minute period. After 5 hours, the reaction is found to be essentially complete with only a trace of starting material remaining.

The reaction is cooled to room temperature and poured into ice water with stirring. The pH (>8) is adjusted to pH 7. The aqueous is extracted well (4 times) with ethyl acetate. The pooled ethyl acetate layers are washed with water, dried (Na$_2$SO$_4$), filtered and evaporated to give a dark red oil. The crude product (1.63 g) is chromatographed on 195 g of 40-63 $\mu$m silica gel. The product is obtained in fractions 34-40 (40 ml each) to give 1.03 g (3.50 mmol, 65%) of an oil; $^1$H NMR ($\delta$ CDCl$_3$) 8.59, 7.97-7.05, 4.27, 4.05, 3.98-3.00, and 1.29. TLC (silica gel 40% acetone-methylene chloride): starting material Rf=0.40; product Rf=0.17.

PREPARATION 5

1H-2,3-Dihydro-3-hydroxy-5-(3-pyridylmethyl)-indene-2-carboxylic acid Ethyl Esters Refer to Chart A (conversion of A-4 to A-5).

The keto-ester of Preparation 4 (788 mg, 2.67 mmol) is dissolved in diethyl ether (60 ml). Water (60 ml) is added followed by the addition, in portions over a five minute period, of solid sodium borohydride (640 mg, 16.9 mmol). The mixture is stirred vigorously for one hour and then a TLC on silic gel indicates complete reaction. The reaction mixture is diluted with more ether and the layers are separated. The aqueous is extracted well with ether (3 times). The pooled ether extracts are washed with water (1 time), followed by brine (1 time), dried (anhyd. $Na_2SO_4$), filtered and evaporated to give 797 mg of a colorless oil. The oil is chromatographed on three Merck Lobar size B columns with chloroform-methanol (49-1), fractions which contain 20 ml each are collected. Eluted first is 315 mg of one epimer in fractions 45 and 46; $^1$H NMR ($\delta$ $CDCl_3$) 8.48, 7.63–6.95, 5.32, 4.25, 3.97, 3.89–2.70, and 1.32; mass spectrum 297.1354 ($C_{18}H_{19}NO_3$ requires 297.1365), 279 (100%), 251, 235, 224, and 206 m/e.

Eluted next is a mixture of both epimers. Eluted last is 356 mg of the other epimer in fractions 48–55; $^1$H NMR ($\delta$ $CDCl_3$) 8.49, 7.62–6.97, 5.47, 4.22, 3.96, 3.12 and 1.30; mass spectrum 297.1363, 279, 250, 224 (100%), 208, and 194 m/e. TLC (silica gel, chloroform/methanol/triethylamine 94/5/1): starting material Rf=0.35; first epimer Rf=0.26; second epimer Rf=0.22.

PREPARATION 6

1H-2,3-Dihydro-3-chloro-5-(3-pyridylmethyl)-indene-2-carboxylic acid, Ethyl Ester and 6-(3-Pyridylmethyl)indene-2-carboxylic acid Ethyl Ester The hydroxy ester of Preparation 5 (315 mg, 1.06 mmol) is treated with thionyl chloride (5 ml) at room temperature with stirring. The mixture is heated at 60° C. for 25 minutes. After cooling to room temperature, the excess thionyl chloride is evaporated. The residue is taken up in an ethyl acetate/saturated sodium bicarbonate mixture. The layers are separated and the aqueous is extracted well with ethyl acetate (4 times). The pooled ethyl acetate layers are washed with half-saturated brine, dried (anhyd. $Na_2SO_4$), filtered and evaporated to give an oil (327 mg). The product is found to be a mixture of three compounds by TLC and NMR evidence. The oil (327 mg) is chromatographed on three Merck Lobar size B columns using 75% ethyl acetate-hexane for elution. Fractions which contain 20 ml each are collected. Eluted first is 127 mg of one chloro isomer. $^1$H NMR ($\delta$ $CDCl_3$) 8.55, 7.67–6.73, 5.68, 4.21, 3.98, 3.69–2.87 and 1.28.

Eluted next is a mixture of the other chloro isomer and the elimination product to give 113 mg. Eluted last is 35 mg of the elimination product; $^1$H NMR ($\delta$ $CDCl_3$) 8.57, 7.83–7.05, 4.28, 4.04, 3.65, and 1.35. TLC (silica gel, 75% ethyl acetate-hexane [run 2 times]: first chloro isomer Rf=0.45; second isomer Rf=0.41; elimination product Rf=0.39.

EXAMPLE 1

6-(3-Pyridylmethyl)indene-2-carboxylic acid Ethyl Ester

Refer to Chart A (conversion of A-6 to A-7).

A solution of the crude chlorination product of Preparation 6 (396 mg, ~0.00128 mole) in benzene (15 ml) is reacted with 1,5-diazabicyclo[4.3.0]none-5-ene (201 mg, 1.6 mmol). The reaction is heated at 40° C. under a nitrogen atmosphere for one hour and then found to be complete by TLC. The reaction is cooled, diluted with ethyl acetate, and water and saturated with $NaHCO_3$ solution (4 ml) are added. The layers are separated and the aqueous is extracted well with ethyl acetate (4 times). The pooled ethyl acetate layers are washed with half-saturated brine, dried ($Na_2SO_4$), filtered and evaporated to give 0.295 g of a dark green oil. The oil is chromatographed on three Merck Lobar size B columns. The solvent used for elution is 30% acetonitrile-methylene chloride. Fractions which contain 20 ml each are collected. The product is obtained in fractions 54–65 to give 256 mg (0.000917 mole, 71%) of a white solid. The solid is recrystallized from pentane to give 221 mg of white crystals (fine needles) mp 74°–74.5° C. Anal. Calcd. for $C_{18}H_{17}NO_2$: C, 77.39; H, 6.13; N, 5.01. Found: C, 77.32; H, 6.16; N, 4.93. High resolution mass spectrum (calcd. for $C_{18}H_{17}NO_2$): 279.1259. Found: 279.1255, other ions at 251, 235, 234, and 206 m/e; IR (nujol mull) 1696, 1694, 1565, 1473, 1422, 1316, 1258, 1202, 1187, 1076, 809, 748, 721, and 713 $cm_{-1}$.

EXAMPLE 2

6-(3-Pyridylmethyl)indene-2-carboxylic Acid

The ester of Example 1 (216 mg, 0.77 mmol) is dissolved in methanol (5 ml) plus water (2 ml) followed by 7.7 ml of 0.1N NaOH. The solution becomes cloudy and a precipitate forms. After three hours more methanol (5 ml) is added and the solution becomes clear. After a total of five hours, the reaction is not complete and there is evidence of methyl ester formation. The reaction is placed under a gentle nitrogen stream overnight to evaporate the methanol.

After 17 hours, the reaction mixture has evaporated to dryness and a white solid is present. TLC indicates that a lot of methyl ester remains. The solid is dissolved in methanol (14 ml) and water (13 ml) is added plus 0.77 ml of 1.0 N NaOH. Stirring is continued at room temperature. After another 72 hours, the reaction mixture is acidified to pH 6.4 with 1.0 NN HCl using pH meter indication. A precipitate forms which is collected by filtration and washed with water. A portion of the precipitate is found to be soluble in ethyl acetate. The ethyl acetate soluble material is recrystallized from ethyl acetate-hexane to give 75 mg, mp 210°–215° C. (decomp.). High resolution mass spectrum (calcd. for $C_{16}H_{13}NO_2$): 251.0946. Found 251.0940; other ions at 222, 207, 191, 150, 129, and 115 m/e.

EXAMPLE 3

6-(3-Pyridylmethyl)indene-2-carboxylic Acid Sodium Salt

The sodium salt of Example 2 is prepared in water by addition of an equivalent of aqueous 0.10N sodium hydroxide. The resulting solution is used for biological evaluation.

EXAMPLE 4

5-[(3-Pyridinylmethyl)amino]-1H-indole-2-carboxylic Acid, Ethyl Ester

Refer to Chart B.

A mixture of 5-amino-1H-indole-2-carboxylic acid, ethyl ester (0.409 g, 2.00 mmol[19], 3-pyridinecarboxaldehyde (0.21 ml, 2.2 mmol), and p-toluenesulfonic acid (42 mg, 0.22 mmol) all in 40 ml of 1:1, glyme:benzene is heated to reflux for 1 hour. Water is collected by use of a Dean-Stark trap. After this time TLC analysis indicates no remaining starting materials. The red colored mixture is allowed to cool and solvents are removed under reduced pressure to give the crude imine as a reddish-brown oil.

TLC (silica gel GF): Rf (imine)=0.23 in 33% acetone/hexane and 0.44 in 50% acetone/hexane.

Without further purification the crude imine is dissolved in 25 ml of absolute ethanol, placed under a nitrogenn atmosphere and cooled to 0°–5° C. (ice bath). To this magnetically stirred solution is added the sodium borohydride (0.23 g, 6.1 mmol) portion-wise over one min. The solution is stirred for 30 min at which time TLC analysis indicates no remaining imine. The reaction is quenched by the addition of saturated aq. ammonium chloride and the ethanol is removed under reduced pressure. The concentrate is diluted with brine and extracted with ethyl acetate (2 times). The organic extracts are combined, dried ($MgSO_4$), filtered and concentrated to give the crude product as a reddish-brown oil. This material is combined with another previously prepared lot of crude material. This crude product is chromatographed on 50 g of HPLC grade silica gel eluting with 40% acetone/hexane and taking 30 ml fractions. Fractions 24–50 are homogeneous by TLC and are combined and concentrated to give 0.63 g of product. This material solidifies and is recrystallized from acetone/hexane to give the titled product as yellow-brown colored needles: mp 178°–179.5° C.

NMR ($d_6$-acetone, TMS): δ 8.84–8.74, 8.64–8.51, 8.04–7.84, 7.50–7.30, 7.07–6.81, 4.46, 4.33, 3.30, and 1.34.

Infrared (nujol): νmax 3325, 3268, 1682, 1629, 1529, 1426, 1348, 1243, 1228, 1192, 1024, 825, 771, and 739 cm$^{-1}$.

Anal. calcd. for $C_{17}H_{17}N_3O_2$: C, 69.13; H, 5.80; N, 14.23. Found: C, 69.21; H, 5.85; N, 14.19.

Mass spectrum: Calcd. for $C_{17}H_{17}N_3O_2$ (M+): 295.1321. Found: 295.1314. Other ions at m/e 249, 203, 157, 130, and 92.

TLC (silica gel GF): Rf=0.32 in 50% acetone/hexane.

EXAMPLE 5

5-[(3-Pyridinylmethyl)amino]-1H-indole-2-carboxylic Acid, Sodium Salt

Refer to Chart B.

The ethyl ester of Example 4, 57.7 mg, 0.195 mmol is dissolved in 4 ml of absolute ethanol. Water (1 ml) and 1.00N NaOH reagent (0.200 ml, 0.200 mmol) are then added. After stirring a total of 70 hours at room temperature TLC still indicates a trace of unhydrolyzed starting material. The solution is diluted with distilled water and washed with ether/methylene chloride. The aqueous phase is filtered through a cotton plug, frozenn and lyophilized to give 47.9 mg of titled product as a gray colored powder.

PREPARATION 7

2-[(3'-Pyridinylmethyl)phenylhydrazono]propanoic Acid Ethyl Ester and 3-Oxo-2-[(3'-Pyridinylmethyl)phenylhydrazono]-butanoic Acid Ethyl Ester Refer to Chart C.

4-(3'-Pyridinylmethyl)aniline (9.20 g, 0.050 mole) is dissolved in water (25 ml) containing concentrated aqueous HCl (10 ml). The solution is cooled (ice bath) and sodium nitrite (3.45 g, 0.050 mole) is added. The mixture is swirled and kept cool on ice. The sodium nitrite dissolves and the solution becomes reddish in color. After 15 min, sodium acetate (15 g) is added followed by ethyl 2-methylacetoacetate (7.0 ml, 7.0 g, 0.0500 mole). The mixture is kept at ice bath temperature and then stored in the refrigerator for 64 hr. The mixture now consists of an aqueous phase and a semi-crystalline, gummy material. The aqueous phase is decanted and the semi-crystalline residue is partitioned between aqueous sodium carbonate (sufficient amount to remain alkaline to pH paper) and ethyl acetate. The ethyl acetate extract is dried ($MgSO_4$), filtered, and concentrated. The residue is taken up in acetone (50 ml) and hexane (50 ml was added. The brown, crystalline precipitate (1.115 g) is collected and by TLC and NMR is found to be primarily the titled product compound. The remaining solution is chromatographed on silica gel (500 g) packed with 30% ethyl acetate-hexane. Fractions of 150 ml are collected.

Fractions 34–36 are crystallized and are pooled and recrystallized from acetone-hexane, giving 1.660 g (total 2.775 g, 0.0093 mole, 18%) of titled product, mp 180°–183° C. Another recrystallization from acetone-hexane gives pale yellow crystals, mp 183°–185° C. (preceded by softening); IR (nujol) 3206, 3158, 3112, 3077, 1688, 1612, 1584, 1508 cm$^{-1}$; $^1$H NMR ($CDCl_3$, δ) 8.52, 7.93, 7.51, 7.00–7.35, 4.31, 3.94, 2.10, and 1.37; high resolution mass spectrum 297.1471, 223, and 182 m/e.

Anal. calcd. for $C_{17}H_{19}N_3O_2$: C, 68.66; H, 6.44; N, 14.13. Found: C, 68.58; H, 6.38; N, 13.90.

EXAMPLE 6

5-(3'-Pyridinylmethyl)indole-2-carboxylic Acid Ethyl Ester

The crystalline product of Preparation 7 (0.50 g, 0.00168 mole) is mixed with polyphosphoric acid (excess) under $N_2$ in a 250 ml round-bottomed flask. The flask is placed in a 90° C. oil bath and the mixture is stirred frequently with a heavy glass rot. After 10 min, the reaction is quenched by addition, in portions, of aq. 10% $Na_2CO_3$ until alkaline to pH paper. The resultin mixture is extracted with ethyl acetate (3 times), the extract is dried ($MgSO_4$), filtered, and concentrated. The crude product crystallizes but is further purified by chromatography over silica gel (50 g, 30% acetone-hexane, 25 ml fractions). The product 0.282 g, 0.001005 mole, 60%) is eluted in fractions 13–17 while fractions 18 and 19 (0.067 g) contain the product and some starting material. Recrystallization of pooled fractions 13–17 from acetone-hexane gives pale yellow crystals (0.226 g) of titled product, mp 158°–160° C. A second recrystallization gives title product as pale yellow crystals, mp 156°–158°; IR (nujol) 3090, 1708, 1578, and 1542$^{-1}$; $^1$H NMR ($CDCl_3$, δ) 9.32, 8.55, 7.03–7.68, 4.41, and 1.42; high resolution mass spectrum, 280.1208, 234, 207, 206, and 205.

Anal. calcd. for $C_{17}H_{16}N_2O_2$: C, 72.84; H, 5.75; N, 9.99. Found: C, 72.73; H, 5.72; N, 9.82.

EXAMPLE 7

5-(3'-Pyridinylmethyl)inolde-2-carboxylic Acid Sodium Salt

The ester of Example 6, (0.112 g, 0.0040 mole) is dissolved in methanol (4 ml). Aqueous 0.10 N sodium hydroxide (4.0 ml, 0.0040 mole) is added and causes partial crystallization of the product. The mixture is warmed on a steam bath until a clear solution is attained. TLC (40% acetone-hexane) shows a heavy spot at the origin and a fluorescent (in UV light) spot just slightly more polar than the product, presumably the methyl ester. After 24 hours, additional water is added (3–4 ml) with the result that a few crystals form in a slightly cloudy solution. The mixture is warmed again on the steam bath but a few crystals remained undissolved. After another 24 hours, addition of water does not cause any more crystallization. TLC shows ester(s) (in solution) are essentially gone. The remaining crystals (0.009 g) are removed by filtration and the filtrate is concentrated under reduced pressure. The residue (0.103 g, 0.000376 mole, 94%) is an off-white glass.

FORMULAS

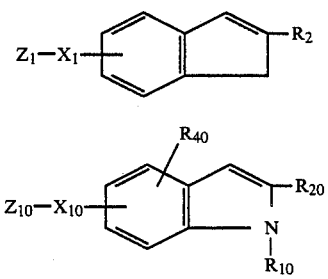

CHART B

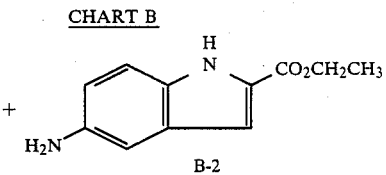

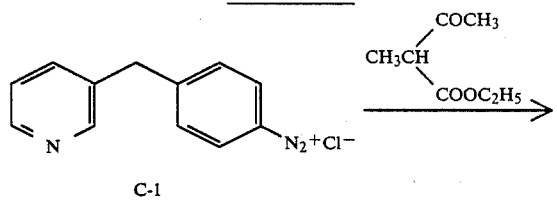

CHART C

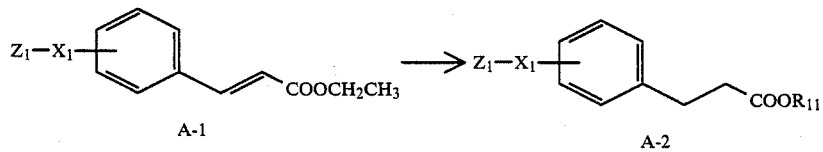

CHART A

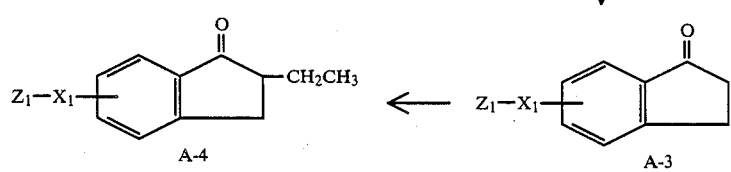

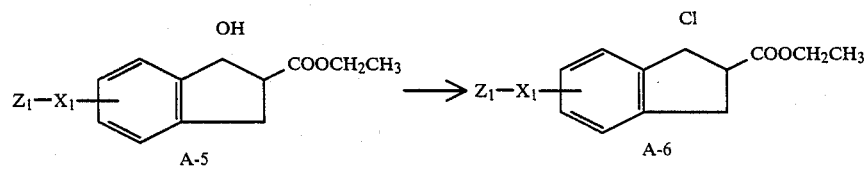

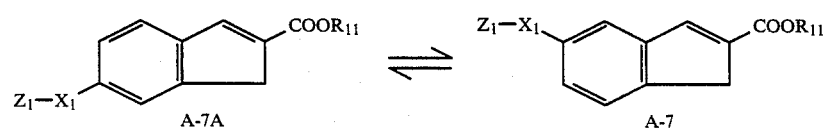

-continued
CHART C

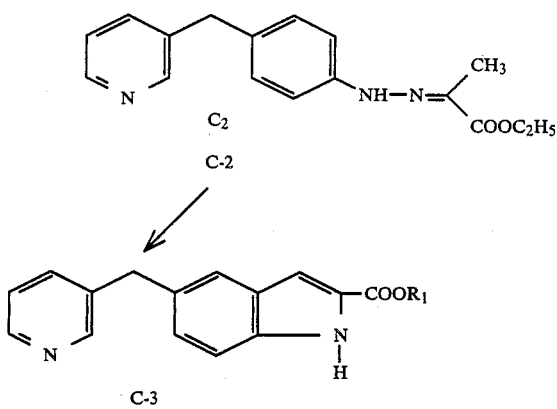

We claim:
1. A compound of the formula II

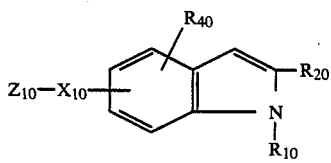

wherein $Z_{10}$ is
(a) 4-pyridinyl, or
(b) 3-pyridinyl;
wherein $X_{10}$ is:
(a) $-(CH_2)_n-$, or
(b) $-CH_2NH-$;
wherein $R_{10}$ is:
(a) hydrogen,
(b) methyl, or
(c) benzyl;
wherein $R_{20}$ is $COOR_3$;
wherein $R_3$ is:
(a) hydrogen,
(b) a pharmacologically acceptable cation, or
(c) $(C_1-C_4)$alkyl;
wherein $R_{40}$ is:
(a) $(C_1-C_4)$alkyl,
(b) chloro,
(c) bromo,
(d) $OCH_3$, or
(e) hydrogen;
wherein $R_{50}$ is:
(a) hydrogen, or
(b) $(C_1-C_4)$alkyl;
wherein n is an integer from 1 to 2; or a pharmacologically acceptable salt thereof.
2. A compound of claim 1, wherein $X_{10}$ is $-CH_2-NH-$.
3. 5-[(3-Pyridinylmethyl)amino]-1H-indole-2-carboxylic acid, ethyl ester, a compound of claim 2.
4. 5-[(3-Pyridinylmethyl)amino]-1H-indole-2-carboxylic acid, sodium salt, a compound of claim 2.
5. A compound of claim 1, wherein $X_{10}$ is $-(CH_2)_n-$.
6. 5-(3'-Pyridinylmethyl)indole-2-carboxylic acid ethyl ester, a compound of claim 5.
7. 5-(3'-Pyridinylmethyl)indole-2-carboxylic acid sodium salt, a compound of claim 5.

* * * * *